United States Patent [19]

Seidel et al.

[11] Patent Number: 4,908,354

[45] Date of Patent: Mar. 13, 1990

[54] PROCESS FOR THE SELECTIVE EXTRACORPOREAL PRECIPITATION OF LOW-DENSITY LIPOPROTEINS

[75] Inventors: Dietrich Seidel, Göttingen; Heinrich Wieland, Freiburg; Gerhard Rosskopf, Fuldabrück-Dörnhagen; Wolfgang Feller, Melsungen-Obermelsungen, all of Fed. Rep. of Germany

[73] Assignee: B. Braun-SSG AG, Emmenbrucke, Switzerland

[21] Appl. No.: 124,394

[22] Filed: Nov. 20, 1987

Related U.S. Application Data

[63] Continuation of Ser. No. 744,199, Jun. 13, 1985, abandoned.

[30] Foreign Application Priority Data

Jun. 16, 1984 [DE] Fed. Rep. of Germany ....... 3422407

[51] Int. Cl.[4] ...................... C07K 15/16; A61K 37/02
[52] U.S. Cl. ......................................... 514/21; 436/86; 436/87; 514/54; 514/55; 514/56; 514/61; 530/359
[58] Field of Search .................... 530/359; 514/21, 54, 514/55, 56, 61; 436/86, 87

[56] References Cited

U.S. PATENT DOCUMENTS

| | | | |
|---|---|---|---|
| 3,920,625 | 11/1975 | Andersson et al. | 260/112 B |
| 4,045,176 | 8/1977 | Proksch et al. | 260/112 B X |
| 4,096,136 | 6/1978 | Ayers et al. | 260/112 B |
| 4,103,685 | 8/1978 | Jupien et al. | 260/112 B X |
| 4,110,077 | 8/1978 | Klein et al. | 260/112 B X |
| 4,287,180 | 9/1981 | Thomas | 424/101 |
| 4,309,188 | 1/1982 | Bentzen | 260/112 B X |
| 4,473,553 | 9/1984 | Zuffi et al. | 424/101 |

FOREIGN PATENT DOCUMENTS 3135814 3/1983 Fed. Rep. of Germany .

Primary Examiner—Howard E. Schain
Attorney, Agent, or Firm—Kenyon & Kenyon

[57] ABSTRACT

A method of precipitating low-density lipoproteins which comprises administering to a volume of blood, plasma or solutions containing blood or plasma a therapeutically or diagnostically effective amount of a low-density lipoprotein precipitating substance at an acid pH such that an anticoagulent effect associated with heparin is minimized or eliminated. The substances utilized in such a method include hydrolyzed heparin, hydrolyzed heparin acylated at free amine groups, sulfated glycosamino glycan and sulfated polysaccharides.

15 Claims, 14 Drawing Sheets pH-dependence of the LDL-precipitation with SP 54® (0.93 g/Liter acetate buffer)

ph-dependence of the supernatant cholesterol on the amount of SP 54 (o) dissolved in the acetate buffer in comparison with heparin (•)

pH-dependence of the supernatant cholesterol on the amount of Arteparon® (o) dissolved in acetate buffer in comparison with heparin (•).

pH-dependence of the supernatant cholesterol on the amount of the chondroitin sulfate from Ligamentum nuchae (Δ) dissolved in acetate buffer in comparison with heparin (●).

PROCESS FOR THE SELECTIVE EXTRACORPOREAL PRECIPITATION OF LOW-DENSITY LIPOPROTEINS

This application is a continuation of application Ser. No. 744,199, filed June 13, 1985, now abandoned.

BACKGROUND OF THE INVENTION

Disease processes connected with a disturbed fat metabolism or an elevated plasma lipid concentration which lead to an abnormal accumulation of lipoproteins, particularly low density lipoproteins, are associated with the development of atherosclerosis (Robin and Angell, Basic Pathology, pps. 271–274, 2nd Ed., 1976) since approximately two-thirds of the total cholesterol is transported in the blood of the normal patient as low density lipoproteins. Thus, a selective separation of beta-lipoproteins or low density lipoproteins (LDL) should result in a consequent decrease in the blood cholesterol level and consequently, a decrease in the threat of the development of atherosclerosis. This is particularly applicable in the case of genetic LDL-receptor defects or defects in the lipid metabolism, particularly familial hypercholestemia type II, which are responsible for an elevated LDL level.

Previous attempts to remove excess LDL from the patient have proven unsatisfactory. For example, a process is described in German Offenlegensschrift DE-OS 31 35 814 according to which the low-density lipoproteins in extra corporeal circulations can be precipitated from human plasma or serum with heparin at acidic pH-levels. This process has a disadvantage in that the heparin level required for this therapeutic treatment is relatively high and thus introduces a risk of hemorrhage. In addition to this, relatively large amounts of the rather expensive heparin, which is not available as a natural product in unlimited quantities, is needed for each treatment.

Thus, there remains a need for a substance that will precipitate LDL without the dangerous side effects or high cost associated with heparin.

SUMMARY OF THE INVENTION

Thus, it is an object of the present invention to provide a process for the replacement of natural heparin with other, more readily available substances or groups of substances for use in the precipitation of low density lipoproteins (LDL) in the acid pH range.

It is another object of the invention to provide a process to precipitate LDL using substances possessing an anticoagulant action that is markedly weaker than that of heparin.

These and other objects are achieved by a method of precipitating low density lipoproteins which comprises administering to a volume of blood, plasma or a solution of blood or plasma a therapeutically or diagnostically effective amount of a low density lipoprotein precipitating substance at an acid pH such that the anticoagulent effect associated with heparin is minimized or eliminated.

More specifically, the invention contemplates a method of precipitating low-density lipoproteins which comprises administering to a volume of blood, plasma or a solution of blood or plasma a therapeutically or diagnostically effective amount of a low-density lipoprotein precipitating substance selected from the group consisting of hydrolyzed heparin, hydrolyzed heparin acylated at free amine groups, sulfated glucosamino glycan and sulfated polysaccharides at a pH in the range of about 4.0 to 5.8 such that the anticoagulent effect associated with heparin is minimized or eliminated.

Thus, the objects of the invention are achieved by the use of polymeric, polyanionic heparin derivatives and other sulfated acid mucopolysaccharides, e.g., glycosamino glycan, as well as polymeric, polyanionic sulfates of sugars, for the specific precipitation of LDL in the acidic pH range without the need for additional adjuvants, e.g., polyvalent cations. Such compounds effectuate precipitation of LDL from the blood thereby simulating the action of heparin while at the same time eliminating the cost and hemorrhagic side effects associated with the use of heparin for this purpose.

DETAILED DESCRIPTION OF THE INVENTION

Figure 1:
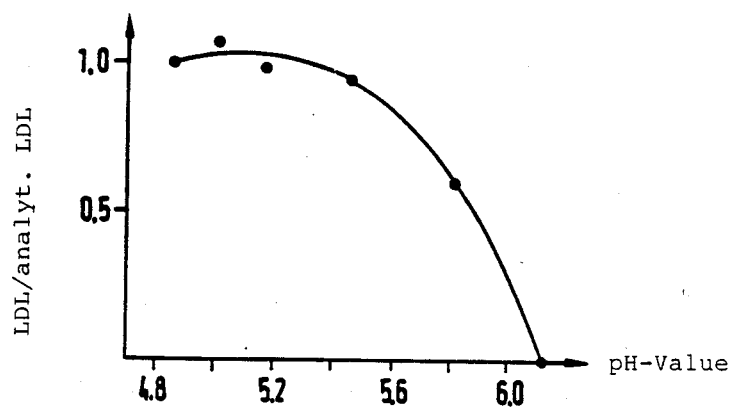
FIG. 1 shows the dependence on pH of the LDL precipitation method according to the invention.

It has now been determined that polymeric, polyanionic heparin derivatives and other acid mucopolysaccharides (glycosamino glycans) as well as polymeric, polyanionic sulfates of sugars are suitable for the specific precipitation of LDL in the acid pH-range without the need for additional adjuvants, e.g. polyvalent cations.

Thus, the invention relates to the use of substances which precipitate LDL while minimizing or eliminating the hemorrhagic effects of heparin. The substances may be derived from heparin or other synthetic or natural compounds. In general, the substances to be used in connection with the process of the invention may be classified as follows:

(a) compounds synthesized from natural heparin by hydrolysis under mild reaction conditions;

(b) compounds synthesized from natural heparin by hydrolysis under mild reaction conditions and subsequent acylation of the free amine groups;

(c) compounds prepared by the sulfation of synthetic or semisynthetic glycosamino glycan; and (d) compounds prepared by the sulfation of natural or synthetic polysaccharides which exhibit a similarity to heparin in that they show a low activity in contrast to heparin when in coagulation-relevant, heparin-sensitive test systems, e.g. thrombin time, partial thromboplastin time or heparin test procedures given in pharmacopeias, but cause a measurable influence on the coagulation system with an activity greater than 1.0 IU/mg, for the selective extracorporeal precipitation of low-density lipoproteins from whole serum or plasma at a pH between about 4.0 and 5.8.

The heparin derivatives mentioned under (a) and (b) above are described in detail in German Offenlegensschrift P 34 22 518.8 entitled "Heparin Derivatives, Process for Their Preparation, Pharmaceuticals Containing These and Their Use for the Treatment of Disturbances of the Fat Metabolism".

The heparin derivatives of (a) above, which can be synthesized from natural heparin by hydrolysis, can be prepared by the acid hydrolysis of heparin and/or its salts under mild, controlled conditions with aqueous 0.2–0.3 M acid at 45° to 70° C. and a pH in the range from 1.5 to 5.0 for 90 minutes to 30 hours, interrupting the reaction by cooling to between 0° and 30° C. and adjusting the pH to between about 6.0 and 8.0 by the addition of an alkali. This is followed by dialyzing the reaction product against water and drying by known methods. Such derivatives are generally characterized by the following parameters:

(a) Appearance: white, amorphous, slightly hygroscopic substance;

(b) content of free amine groups: 50 to 400 $\mu$mol/g;

(c) ratio of content of uronic acid and hexosamine: 0.97 to 0.995;

(d) specific rotation: $(\alpha)_D^{20} = +35$ to $+60°$;

(e) coagulation activity: about 1.0 to 20 IU/mg;

(f) metachromatic dye effect relative to heparin (=1.0): 0.10 to 0.90 (measured with toluidine blue);

(g) mean molecular weight: 2,000 to 30,000 D;

(h) suitability as substrate for heparinase (EC 4.2.2.7) from Flavobacterium heparinum: reaction rate at substrate saturation (at 30° C. and pH 7.0), relative to the heparin used for the preparation (=100%): 10% to 100%;

(i) binding to antithrombin III (AT III): no portion with high binding affinity (high-affinity heparin) was found in comparison with the heparin used for the preparation in an affinity chromatographic separation over human-antithrombin III bound to Sepharose ®, while the portion with low affinity (low-affinity heparin) is always smaller than in the heparin used for the preparation;

(j) IR-Spectrum: increase in the intensity of the bands at 1130 to 1160 cm$^{-1}$ relative to the heparin used for the preparation;

(k) $^{13}$C-NMR spectrum: decrease in the intensity of the signals at 97.8 and 58.7 ppm; increase in the intensity of the two pH-dependent signals at 92.1 to 97.8 ppm and 55 to 56 ppm relative to heparin;

(l) $^1$H-NMR spectrum (400 MHz): decrease in the intensity of the signal at 3.25 ppm (A-2s) in comparison with the signal at 3.40 ppm (A-2s) relative to heparin.

The heparin derivatives mentioned under letter (b) above, which are acylated at the free amine groups of the hydrolyzed heparin derivative, are obtained by the acid hydrolysis of heparin and/or its salts under mild, controlled conditions with aqueous 0.2–0.3 M acid at about 45° to 70° C. and a pH in the range from about 1.5 to 5.0 for 90 minutes to 30 hours, interrupting the reaction with cooling to between 0° C. and 30° C. and adjusting the pH to about 6.0 to 8.0 by the addition of an alkali, dialyzing the reaction product against water, drying by known methods and acylating the obtained product at the free amine groups.

The acyl derivatives of letter (b) above are generally characterized by the following parameters:

(a) Appearance: white, slightly hygroscopic substance;

(b) content of free amine groups: 2 to 10 $\mu$mol/g;

(c) ratio of content of uronic acid and hexosamine: 0.97 to 0.995;

(d) specific rotation: $(\alpha)_D^{20} = +30$ to $+60$;

(e) coagulation activity: about 10–20 IU/mg;

(f) metachromatic dye effect in comparison with heparin (=1.0): 0.10 to 0.90 (measured with toluidine blue);

(g) mean molecular weight: 2,000 to 30,000 D;

(h) suitability as substrate for heparinase (EC 4.2.2.7) from Flavobacterium heparinum: reaction rate at substrate saturation (at 30° C. and pH 7.0), relative to the heparin used for the preparation (=100%): 10 to 100%;

(i) binding to antithrombin III (AT III): an affinity chromatographic separation over human antithrombin III bound to Sepharose ® did not show any portion with high binding affinity (high-affinity heparin) relative to the heparin used for the preparation, while the portion with low affinity (low-affinity heparin) was always smaller than the heparin used for the preparation;

(j) $^1$H-NMR-Spectrum (400 MHz): approximately identical signal intensity at 3.25 and 3.40 ppm in the case of acetylation.

The LDL-precipitating substances mentioned under letters (c) and (d) above, which can be prepared by sulfation of synthetic or semisynthetic glycosamino glycans or by sulfation of natural or synthetic polysaccharides, are prepared by known methods. The following compounds are exemplary, most of which are commercially available:

1. Sodium salt of chondroitin sulfate from shark cartilage (supplied by CalbiochemBehring Corp., La Jolla);

2. sodium salt of chondroitin sulfate from bovine ligamentum nuchae (supplied by: Serva, Heidelberg);

3. sodium salt of heparin sulfate from pig mucosa (supplied by: Calbiochem-Behring Corp., La Jolla; preparation according to B. Casu et al., Pharmacol. Res. Commun. 11: 279, 1979);

4. sodium salt of dermatan sulfate from pig mucosa (supplied by: Calbiochem-Behring Corp., La Jolla;

preparation according to: B. Casu et al., Pharmacol. Res. Commun. 11: 279, 1979);

5. sodium pentosan polysulfate, mean molecular weight: approx. 2,000 (SP 54 ®, supplied by: Bene Chemie, Munich);

6. mucopolysaccharide polysulfuric acid ester (Arteparon ®, supplied by: Luitpold-Werk, Munich);

7. sodium pentosan polysulfate, mean molecular weight: 4,000 (Thrombocid ®, supplied by: Bene-Chemie, Munich);

8. heparinoid Bayer 5000 HDB-E: the heparinoid is contained in the pharmaceutical preparations Bayolin ® Liniment, Bayropharm and Lasonil ®, Bayer-Leverkusen;

9. mucopolysaccharide polysulfuric acid ester from Ateroid ® (supplied by: Dr. Rentschler, Laupheim);

10 sodium salt of the polyanethol sulfonic acid (supplied by: Serva, Heidelberg);

11. heparin derivatives prepared on a base of chitosan (synthesis according to: M. L. Wolfrom et al., Journal American Chemistry Society 81: 1764 ff., 1959);

12. heparinoid on a base of xylane (synthesis according to: V. M. Doctor, V. Sauls, Thrombos. Res. 30: 573-578, 1983);

13. heparinoids on a base of dextran (dextran sulfate) (synthesis according to: C. R. Recketts, Biochem. J. 51: 129-133, 1952);

14. heparinoids derived from alginic acid (synthesis according to: O. Larm et al., Carbohydrate Research 73, 332-36 (1979);

15. heparinoids on a base of cellulose sulfate (synthesis according to: G. Kindness et al., Br. J. Pharmac. 68: 645-649, 1980);

16. heparinoids on a base of sulfated Ncarboxymethyl chitosan (synthesis according to: R.A.A. Muzzarelli, Polymer Science and Technology, 23: 359-374, 1983) or 17. synthetic heparinoids (synthesis according to: M. Okada et al., Makromol. Chem. 180: 813-817, 1979 and H. Komoda, Makromol. Chem. 181: 2305-2314, 1980).

These LDL-precipitating substances of the invention remain unchanged for years and can be stored while retaining their full activity when they are in the form of sterile, aqueous solutions, with the addition of known solvents, stabilizing agents and/or preservatives such as benzyl alcohol, or as solids. They can also be sterilized by known methods such as sterile filtration or steam or heat sterilization, for example, at 105° to 121° C. for 30 minutes.

Their anticoagulant activity makes the LDL-precipitating substances of the invention particularly suitable for intravenous administration in solution form. They can also be made available as pharmaceutical substances for extra corporeal precipitation after adjusting the pH of the blood, plasma or solutions containing blood or plasma to between about 5.0 and 8.0 and an appropriate adjustment of the osmolarity. The preferred application of the LDL-precipitating substances of the invention lies in the selective extra corporeal precipitation of (LDL) from whole blood or plasma at a pH between about 4.0 and 5.8. In general, the LDL-precipitating substances of the invention are suitable for application in the therapeutic field as well as in the area of diagnostic testing.

The process and a device for the selective extra corporeal precipitation of LDL from whole blood or plasma are known from German Offenlegensschrift DE-OS 31 35 814, which discloses the use of natural heparin as a precipitating agent. In contrast, the LDL-precipitating substances according to the invention offer the advantage of being able to precipitate LDL while minimizing or eliminating coagulation activity in comparison with heparin. The substances of the invention cause the precipitation of LDL to take place to an extent comparable to that of natural heparin, while the danger of hemorrhage in patients treated with the heparin derivatives is not present because of the low coagulation activity of these heparin replacement substances.

The invention is explained in more detail by the following examples.

EXAMPLE 1

The anticoagulant activities of the substances numbered 1 to 17 above and natural heparin in which the precipitation of LDL was carried out with a process and device according to German Offenlegensschrift 31 35 814 are compiled in Table 1 below. The mentioned compounds were used in the amount of 0.93 g/L in an acetate buffer at a pH of 4.85 for the precipitation experiments, as explained in Example 5, Part C in the description of the experiment. The pH range given in Table 1 characterizes the pH values between which at least 50% of the LDL was precipitated.

The recorded anticoagulant coagulation activity was performed with a test according to USP XX with sheep plasma, or with a chromogenic substrate test, as described, e.g., in Teien et al., Thromb, Res. 8: 413, 1976, and Thromb. Res. 10: 399, 1977. These tests showed that the subject substances—independent of their chemical structure—are suitable as precipitating agents for LDL, with coagulation activities greater than or equal to about 1.0 IU/mg.

TABLE 1

| Results of the LDL precipitation experiments | | |
|---|---|---|
| Sequential # of test substance | pH-Range for the LDL precipitation | Anticoagulation activity (IU/mg) according to USP XX |
| 1 | inadequate precipitation, cf. Ex. 3 | <0.5 |
| 2 | inadequate precipitation, cf. Ex. 3 | <0.5 |
| 3 | 4.2-5.5 | 5 |
| 4 | 4.2-5.5 | 12 |
| 5 | 4.5-5.8 | 17.6 |
| 6 | 4.6-5.8 | 22-35 |
| 7 | 4.4-5.8 | 15.9 |
| 8 | inadequate precipitation | 0.43 |
| 9 | inadequate precipitation | 0.375 |
| 10 | 5.0-5.8* | 5.6 |
| 11 | 4.2-5.8 | 52 |
| 12 | 4.2-5.8 | 23 |
| 13 | 4.2-5.8 | 14 |
| 14 | 4.2-5.8 | 2.8 |
| 15 | 4.2-5.8 | 20 |
| 16 | 4.2-5.8 | 27 |
| 17 | 4.2-5.8 | 6 |
| Heparin-Na (control) | 4.5-5.8 | 155 |

*2.0 g/L precipitating agent

EXAMPLE 2

The heparinoids described herein were tested for their ability to precipitate low-density (LDL) from human plasma. For this, the substances were dissolved in a concentration of 0.93 g/liter in 0.2 M sodium buffer adjusted to pH 4.85 with 500 μl acetic acid. Aliquots of 500 μl human plasma were mixed with 500 μl of the acetate buffer containing the respective test substances.

After standing for 10 minutes at room temperature or 37° C., the mixtures were filtered through a 0.4 μm filter or centrifuged, and the concentration of the supernatant cholesterol was determined. The LDL-cholesterol concentration precipitated by the heparin derivative was obtained after deducting the supernatant cholesterol value from the previously determined total cholesterol content.

In all of the following figures, the precipitated LDL-cholesterol is plotted on the ordinate as quotient of the precipitated LDL/analytical LDL, or the content of supernatant cholesterol is given directly in mg/dl. The analytical LDL-cholesterol value was obtained by the analytical LDL test with heparin citrate solution by H. Wieland, D. Seidel, J. Lipid., Res. 24: 904–909, 1983. A quotient of 1 consequently represents the quantitative precipitation of the LDL-cholesterol.

Figure 2:
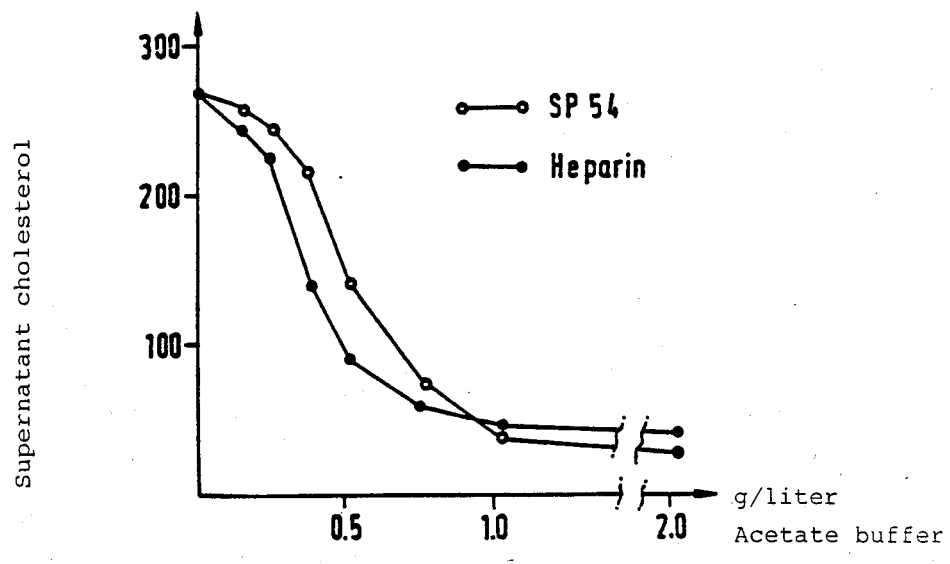
FIG. 2 demonstrates the pH dependence of the supernatant cholesterol level from the amount of an LDL-precipitating substance according to the invention, in comparison to heparin.

The pH values were adjusted to a value in the range of 4.0 to 5.4 by changing the amount of acetic acid in the sodium acetate buffer required for adjustment of the pH. After mixing equal parts per volume of the human plasma with the solution of the subject substance (0.93 g/L), pH values were obtained that are plotted as the abscissa in the enclosed figures; FIG. 1 shows the pH-dependence of the LDL-precipitation with Number 5 of the subject substances (sodium pentosan polysulfate) described above and FIG. 2 shows the decrease in the supernatant cholesterol in dependence on the amount of subject substance Number 5 dissolved in the sodium acetate buffer of pH 4.85.

Figure 3:
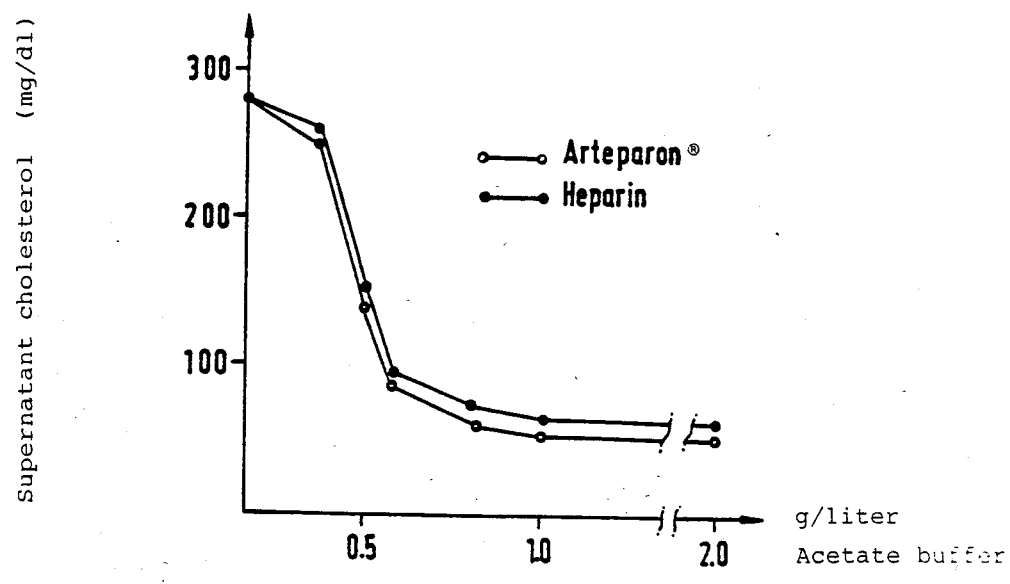
FIG. 3 demonstrates the pH dependence of the supernatant cholesterol level from the amount of LDL-precipitating substance, in comparison to heparin.
Figure 4:
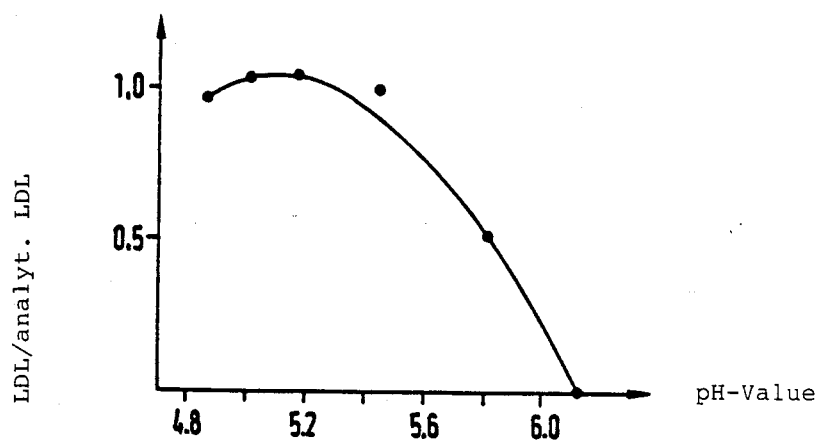
FIG. 4 demonstrates the pH dependence of the LDL precipitation with a LDL-precipitating substance according to the invention.
Figure 5:
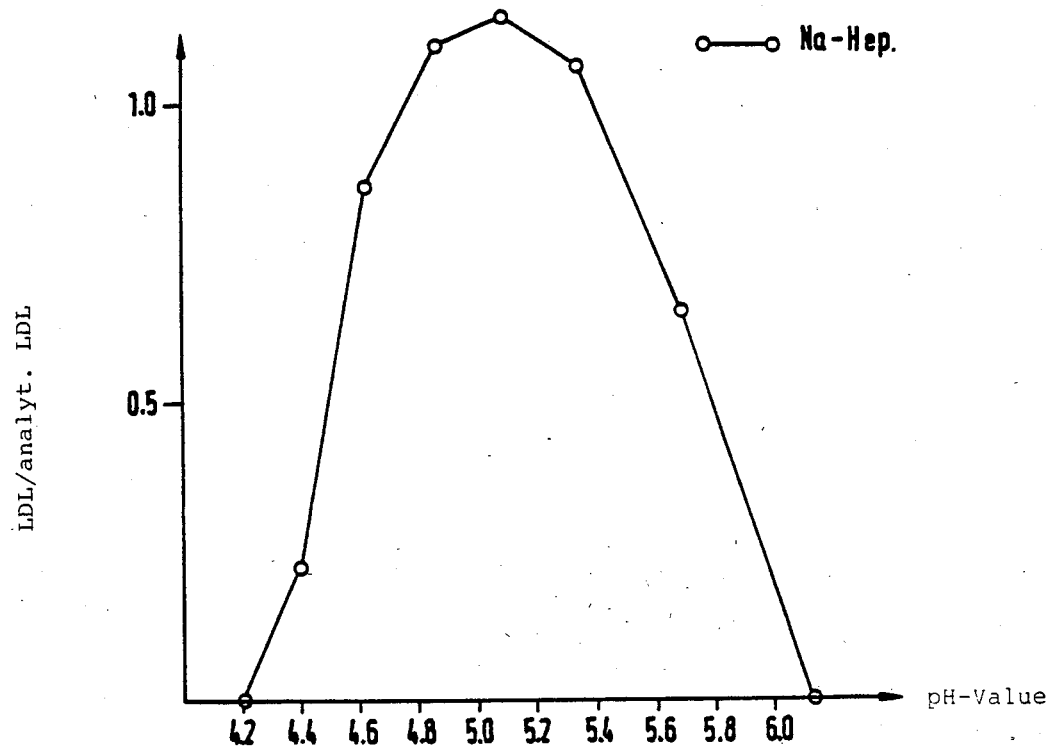
FIG. 5 demonstrates the pH dependence of the LDL-precipitation with sodium heparin.

EXAMPLE 3:

The LDL-precipitation with Arteparon ® was performed according to Example 1. The result of the measurements on the LDL-precipitation dependent on the amount of Arteparon ® dissolved in the acetate buffer is plotted in FIG. 3 in comparison with heparin. The pH-dependence of the LDL-precipitation with Arteparon ® is shown in FIG. 4, while the pH-dependence of the LDL-precipitation with heparin-Na can be found in FIG. 5.

Figure 6:
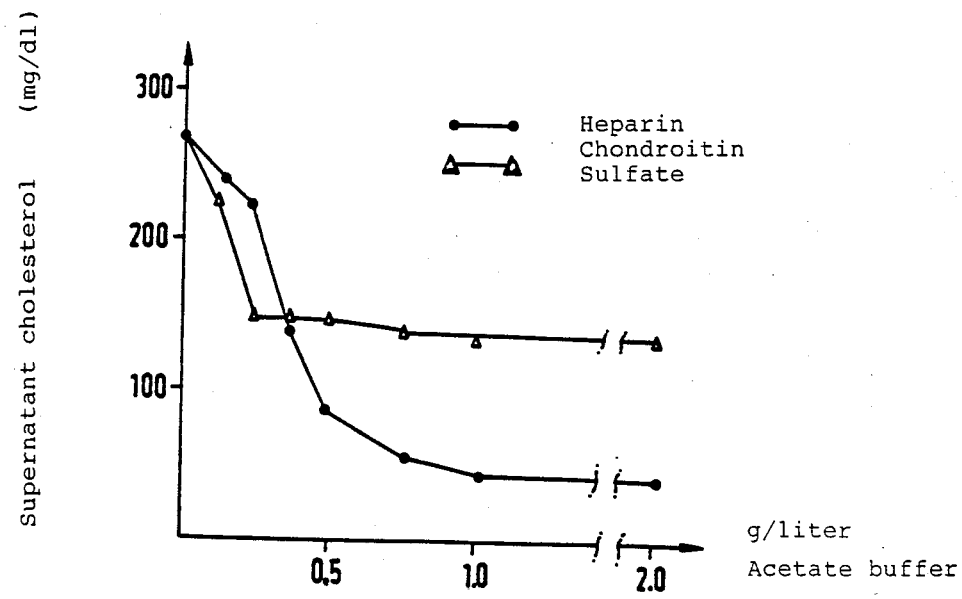
FIG. 6 shows the dependence of the supernatant cholesterol level from the amount of chondroitin sulfate dissolved in acetate buffer, in comparison with heparin.

EXAMPLE 4:

Chondroitin sulfate from bovine ligamentum nuchae was used as LDL-precipitating agent as described in Examples 1 and 2. The results of the measurements are plotted in FIG. 6 showing the dependence of the LDL-precipitation on the amount of chondroitin sulfate dissolved in the acetate buffer, in comparison with heparin. The results show that chondroitin sulfate cannot be used as LDL-precipitating agent under these conditions since the precipitation leads to an inadequate (approx. 40%) reduction of the LDL-content in the plasma.

EXAMPLE 5:

A: Preparation of hydrolyzed heparin

Thirty grams of heparin with a mean molecular weight of 15,000 D was dissolved in 480 ml of distilled, pyrogen-free $H_2O$ and mixed with 240 ml of 1 N hydrochloric acid prewarmed to 70° C. in a reaction vessel. The reaction mixture was maintained at 70° C., and the pH was 1.0. After a hydrolysis lasting 80 minutes, the reaction was interrupted by cooling in an ice bath and the pH of the reaction mixture was adjusted to between 6.8 and 7 by the addition of 30 ml of 5 N sodium hydroxide solution. The reaction product was dialyzed against distilled, pyrogen-free water and spray-dried. Obtained was 25 g of a white, hygroscopic product that had a coagulation activity of 1.9 IU/mg. The activity was tested according to the US-Pharmacopeia XX and expressed in international units. The third international heparin standard was used as a comparison standard.

B: Characteristic Analytical Data of Product A

The uronic acid content in the product was determined according to T. Bitter et al., Analytical Biochem. 4: 330, 1962. The lactone of glucuronic acid was used as a standard. The product had a uronic content of 28.2%. The content of hexosamine groups was determined colorimetrically according to R. E. Hurst et al., Analytical Biochem. 15: 88, 1981. The ratio of the uronic acid content to the content of hexosamine groups was 0.98.

The content of N-acetyl groups in the product, determined by alkaline hydrolysis and titration of the released acetate, was 8.3% (w/w).

The relative content of free amine groups was established with 2,4,6-trinitrobenzene-1-sulfonic acid according to K. Satake et al., J. Biochem. 47: 654, 1960. Glycine was always used as a comparison substance. While the content of free amine groups in commercial heparin is in the range from about 10 to 50 μmol/g, a value of 129 μmol/g was found for the product from Example 5A.

The metachromatic dye effect, i.e. the property of heparin and its derivatives in triggering metachromatic changes of the UV/VIS -spectrum in basic dyes (e.g. toluidine blue) was tested according to Silbert, Biochem. Biphys. Res. Commun. 69: 570, 1976, with heparin and the product from Example 5A. While the strongest effect was measured with heparin, the hydrolyzate exhibited a markedly weaker effect. The slopes of the two linear curves (dependence of metachromatic effect on concentration) are as 1 (heparin) : 0.65.

The rate of reaction of heparinase (E.C. 4.2.2.7) from Flavobacterium heparinum with heparin and its derivatives as substrate is strongly dependent upon the structure of the respective substrate. Conversely, the degree of structural deviation of the substrate from heparin can thus be expressed as the ratio of the heparinase activity of heparin to the activity of the tested derivative. The activity was measured under the following conditions according to A. Linker, Methods in Enzymology 28: 1972 and PCT-patent/US 81/01081: heparinase was isolated from Flavobacterium heparinum by chromatography over hydroxyl apatite and phosphocellulose. Samples of 20 ul heparin or of the heparin hydrolyzate substance (25 mg/ml) and 20 ul heparinase solution were mixed with 2.5 ml of a buffer mixture of 0.25 M sodium acetate solution and 0.025 M calcium acetate solution (pH 7.0). The enzymation reaction was recorded at 30° C. by registering the changes in extinction at 232 nm as a function of time. The slope of the time-/conversion curve of heparin was set at 100%. Preliminary tests ascertained that the reaction took place at substrate saturation. A rate of reaction of 54% relative to heparin was found for the product from Example 5A.

The specific rotation of the starting heparin had a mean of 50.9° ; a specific rotation $(\alpha)_D^{20}$ of 42.5° was found for the product from Example 5A.

The molecular weight or the molecular weight distribution of the hydrolyzate according to Example 5A did not change relative to the heparin used as starting material. A mean molecular weight of 15,000 was determined.

Figure 7:
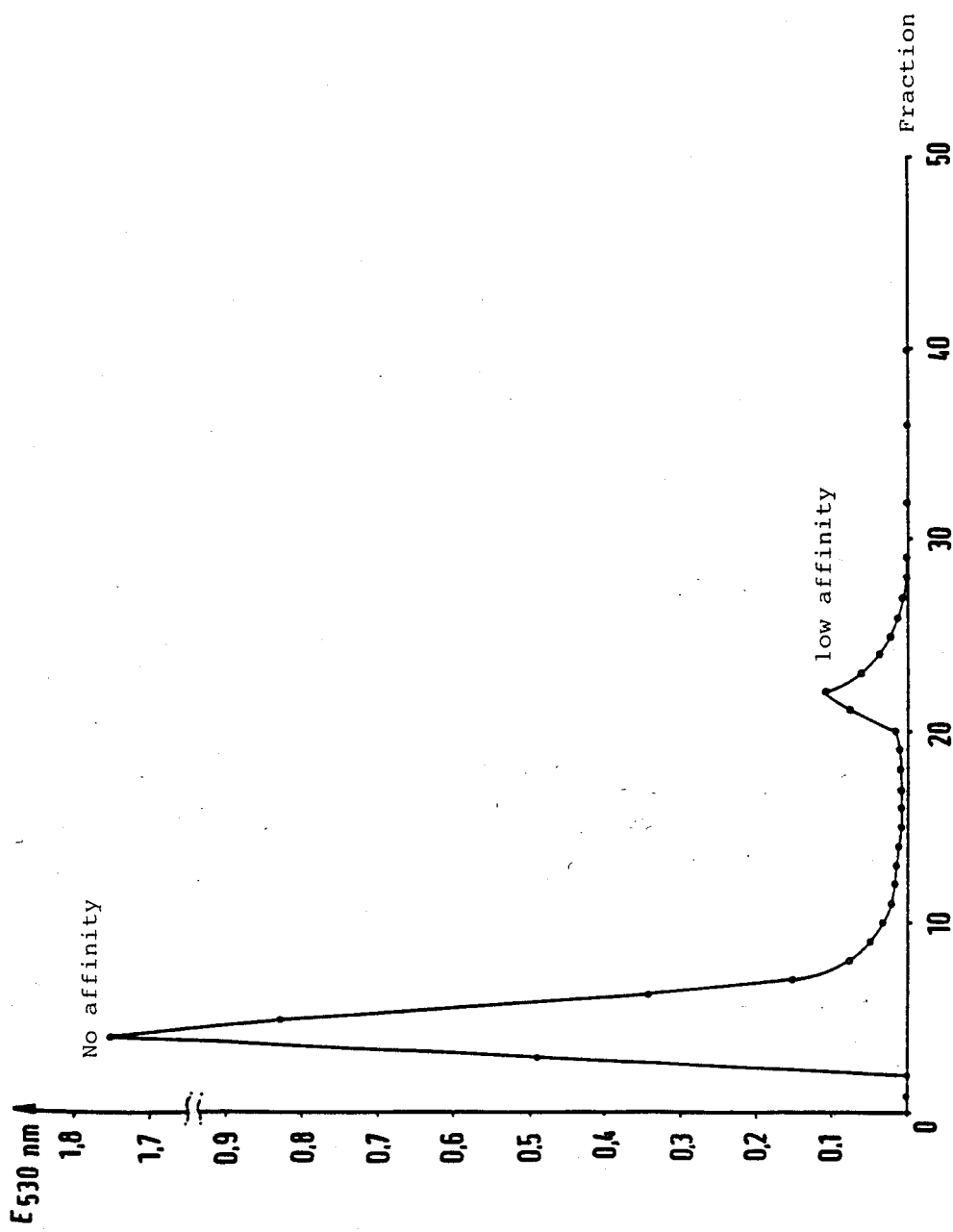
FIG. 7 shows the elution profile of an LDL-precipitating substance in an affinity chromatography over human antithrombin III immobilized on Sepharose ® demonstrating weak or no binding affinity by an LDL-precipitating substance according to the invention.
Figure 8:
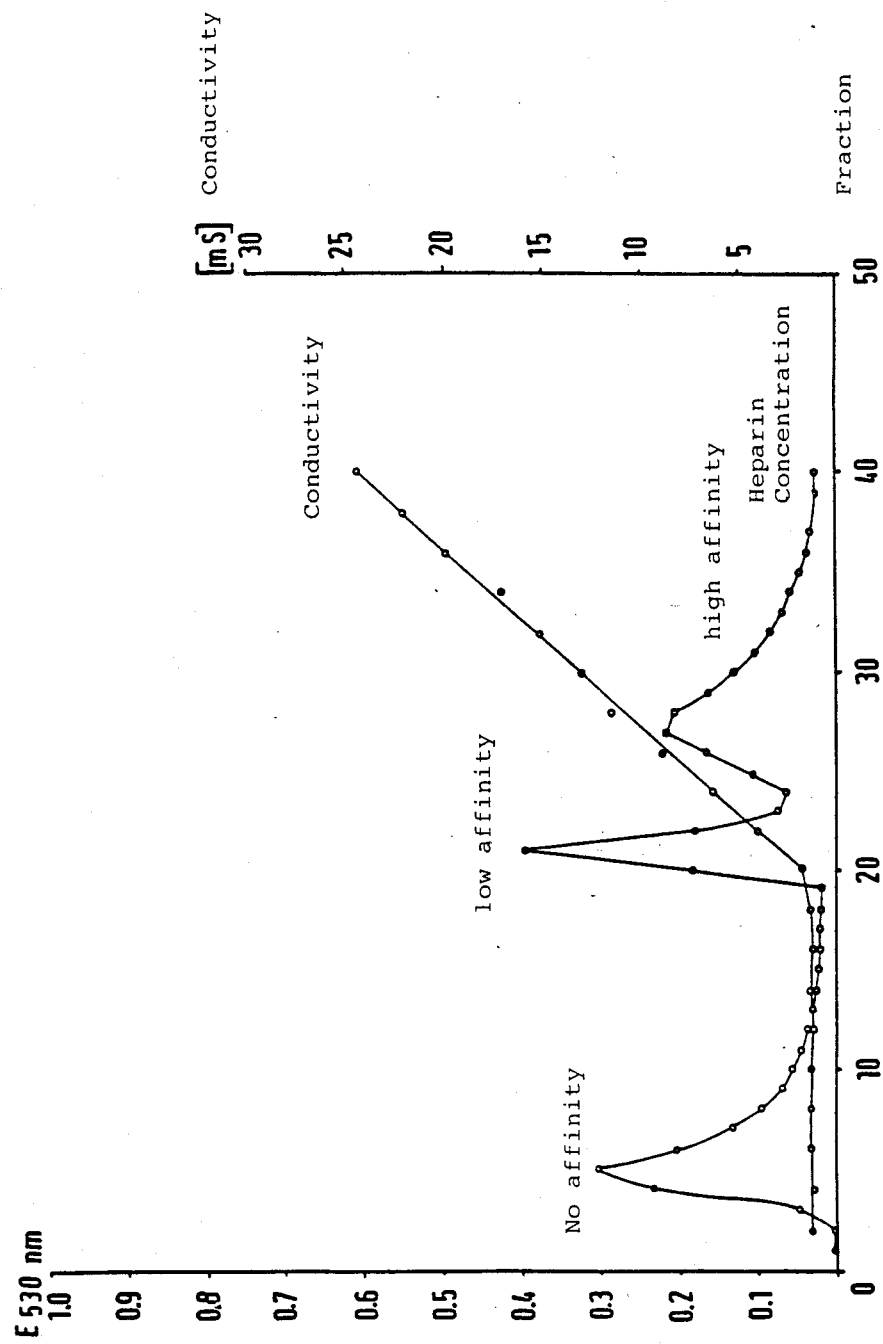
FIG. 8 demonstrates the elution profile of the affinity chromatography of heparin used to prepare the LDL-precipitating precipitating substance of FIG. 7 on antithrombin III/Sepharose ®.

The product of Example 5A was tested for its characteristic of binding to anti-thrombin III in comparison with the starting heparin. Affinity chromatography over human antithrombin III covalently coupled with Sepharose® 4B was performed according to M. Hoock et al., FEBS Letters 66: 90, 1976. This furnished three heparin fractions with different degrees of binding to antithrombin III (nonbinding, weakly binding and strongly binding fraction) for the commercial heparin. The product from Example 5A, in contrast, had only a very small proportion of weakly binding fraction bound to antithrombin III. The elution profile of the affinity chromatography of the product according to the invention on antithrombin III/Sepharose® is shown in FIG. 7, and that of the heparin used for the preparation in FIG. 8. (Conditions of the affinity chromatography on antithrombin III, which was coupled to Sepharose® 4B:

Buffer 1: 0.05 M tris-buffer, 0.05 M NaCl-solution, pH 7.5

Buffer 2: 0.05 M tris-buffer, 2.5 M NaCl-solution, pH 7.5

Elution with (1) 30 ml buffer 1 (2) 30 ml buffer and 30 ml buffer 2 (linear sample)

Rate of flow: 15 ml/hr

Amount of sample: 1.0 ml; 3 mg/ml

Eluate samples of 2 ml each were collected.

The sulfur content of the product from Example 5A decreased in comparison with the heparin used for the preparation from 11.5% to 9.8% (w/w).

The course of the acid hydrolysis was observed with the aid of a heparin-sensitive coagulation test, the activated partial thromboplastin time. For this, samples of 0.8 ml each were removed from the reaction mixture at specific times, neutralized with 5 mM sodium carbonate solution to 0.9% NaCl-solution and diluted to 100 ml with the same buffer. One part by volume of this stock solution was then diluted further with four parts by volume 0.9% NaCl. Aliquots of 50 µl of this dilution were mixed with 950 µl human plasma and the apTT determined with the use of the reagent Pathromtin®, Behringwerke, Marburg.

The ball coagulometer KC 4 by Amelung GmhB, Lemgo, was used for the determination. Table 2 below shows the change in the measured coagulation time as a function of time, in seconds (mean of four measured values) as well as the standard deviation calculated from four measured values each and the coefficient of variation.

TABLE 2

| Coagulation activity of the Heparin hydrolyzate (70° C.) | | | | | | |
|---|---|---|---|---|---|---|
| Reagent blank (without heparin) | Coagulation time (sec.) after a hydrolysis time of | | | | | |
| | 0 min. | 15 min. | 30 min. | 50 min. | 65 min. | 80 min. |
| Mean 43.25 | 213.7 | 135.8 | 92.95 | 50.8 | 48.2 | 43.90 |
| S 0.25 | 0.25 | 0.44 | 0.29 | 0.45 | 0.14 | 0.36 |
| $V_K$ (%) 0.58 | 0.12 | 0.33 | 0.31 | 0.89 | 0.29 | 0.82 |

The product prepared according to Example 5A was tested for its ability to precipitate low-density lipoprotein (LDL) from human plasma. For this purpose, the product from Example 5A was dissolved in a concentration of 0.93 g/liter in 0.2 M sodium acetate buffer adjusted with acetic acid to pH 4 85. A sample of 500 µl human plasma was mixed with 500 µl of the acetate buffer containing the product from Example 5A. After 10 minutes of standing at room temperature, the mixture was filtered through a 0.4 µm filter or centrifuged, and the concentration of the supernatant cholesterol was determined. The LDL-cholesterol concentration precipitated by the heparin derivative was obtained after deduction of the supernatant cholesterol value from the previously determined total cholesterol content.

The precipitated LDL-cholesterol was plotted as the quotient of the precipitated LDL/analytical LDL on the ordinate in the following figures. The analytioal LDL-cholesterol value was determined by the analytical LDL-test with heparin citrate (H. Wieland and D. Seidel, J. Lipid Res. 24: 904, 1983).

Figure 9:
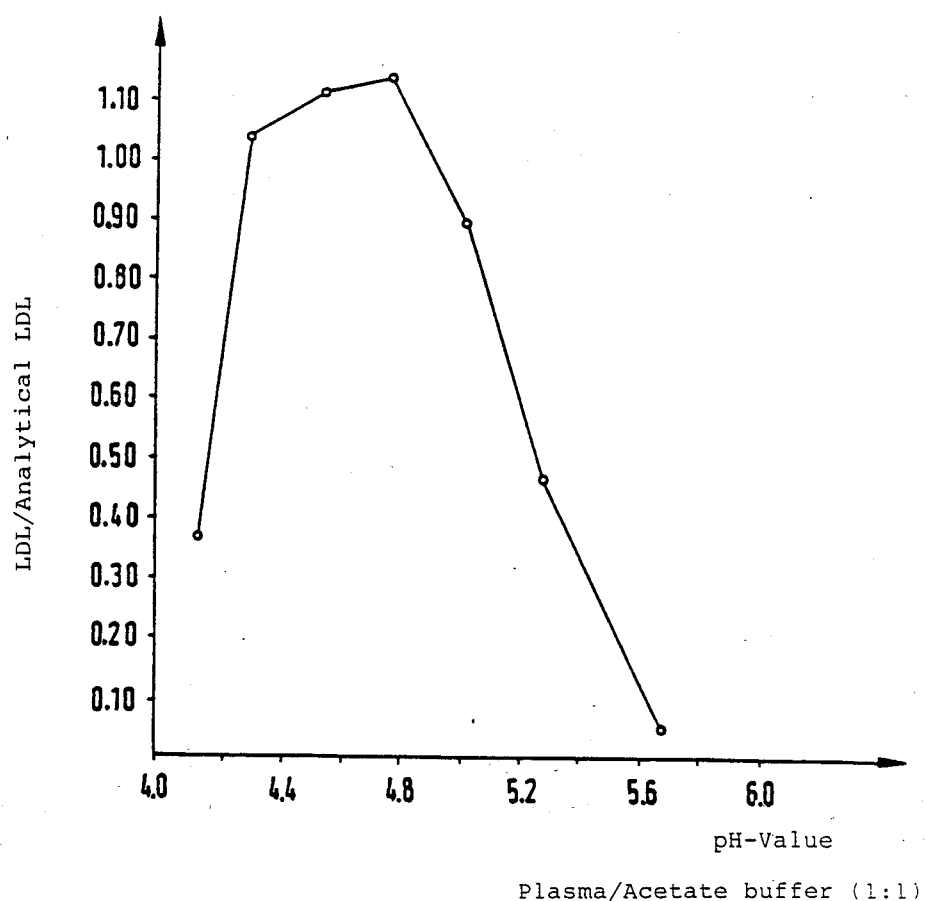
FIG. 9 shows the pH dependence of the LDL precipitation with the LDL-precipitating substance according to the invention.
Figure 10:
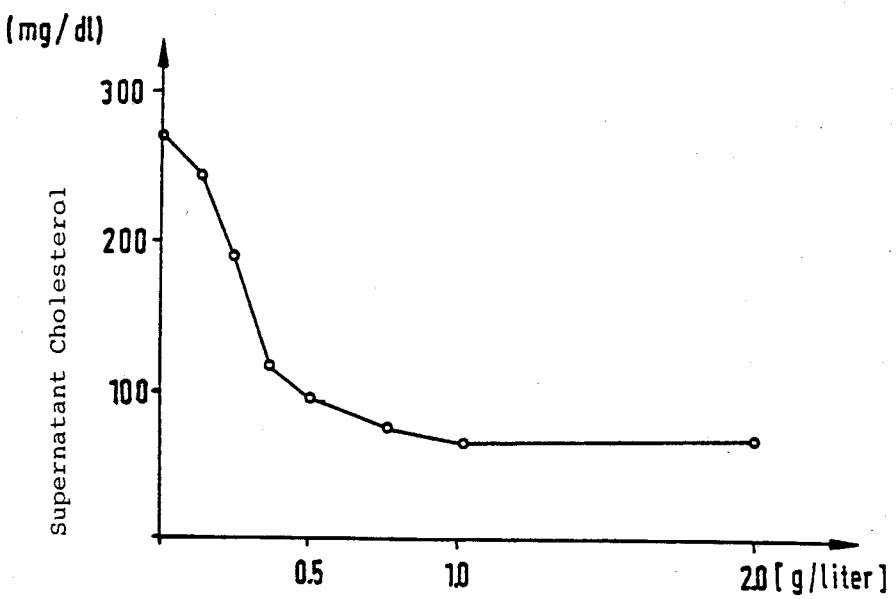
FIG. 10 demonstrates the decrease in the supernatant cholesterol in dependence on the amount of LDL-precipitating substance according to the invention.

A quotient of 1 thus represents the quantitative precipitation of the LDL-cholesterol. Values for pH in the range of 4.0 to 5.4 were obtained by varying the amount of acetic acid required for the adjustment of the pH in the sodium acetate buffer. After mixing equal parts by volume of human plasma with the solution of the heparin derivative (0.93 g/liter) in sodium acetate buffer, pH-values were obtained that are plotted along the abscissa in the following figures. FIG. 9 shows the pH-dependence of the LDL-precipitation with the product from Example 5A. FIG. 10 shows the decrease in the supernatant cholesterol in dependence on the amount of product from Example 5A dissolved in the sodium acetate buffer, pH 4.85.

EXAMPLE 6:

A: Preparation of the Heparin substitute

A heparin hydrolyzate prepared according to the directions given in Example 5A was reacted in a subsequent step with acetic anhydride. The objective of this step was the acetylation, by known methods, of the amine group released by the hydrolysis step.

For this purpose, 2.5 g of a heparin hydrolyzate (prepared according to Example 1) with a low coagulation activity of 5.71 IU/mg (USP XX) was dissolved in 279 ml $H_2O$ and 30 ml methanol and 1.5 g of sodium carbonate was added. Six milliliters of acetic anhydride was added dropwise to this solution over a period of 30 minutes, with cooling on ice. The pH was maintained between 7.0 and 7.5 with 3 M $Na_2CO_3$-solution. The reaction mixture was then agitated for 2 hours in the ice bath and subsequently dialyzed against water for 2 days. The obtained product was precipitated by known methods with ethanol and dried overnight in the vacuum drying cabinet at 60° C. The white, slightly hygroscopic product (yield: 2.1 g) had a coagulation activity of 16.9 IU/mg (USP XX).

B: Characteristic Analytical Data of Product

Figure 11:
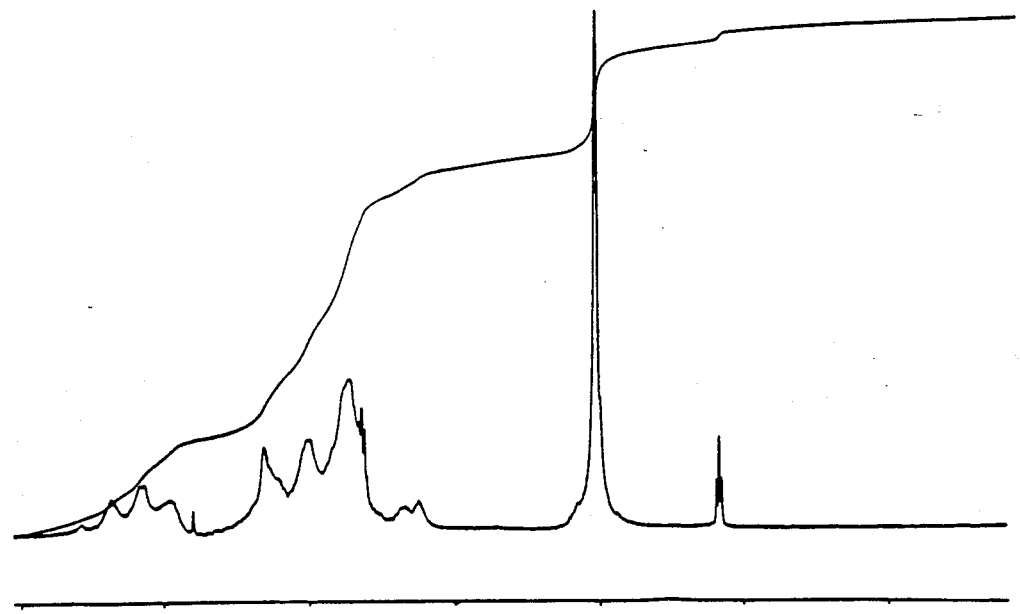
FIG. 11 demonstrates the 400-MHz $^1$H-Spectrum of the LDL-precipitating substance according to the invention.

The 400-MHZ $^1$H-NMR-spectrum of the product from Part A is shown in FIG. 11. The spectrum (50 mg/ml $D_2O$; internal standard: HDO; rel. to TMS:$\delta$=4.8 ppm) has, in comparison to heparin, an elevated peak of the N-acetyl signal. The product contains—as can be seen from the spectrum—some ethanol as a contaminant (1.18, 3.59 ppm). The content of free amine groups decreases from 145 µmol/g in the starting material to 4.4 µmol/g. The rate of cleavage with heparinase changes from 53% (heparin=100%) of the starting material to 45% with the acetylated product.

The specific rotation changes from $(\alpha)_D^{20}$=+51° to 44.5°. The metachromatic effect, measured with toluidine blue, changes from 85% of the starting material to 82% relative to heparin (+100%).

C: Use for the LDL-Precipitation

Figure 12:
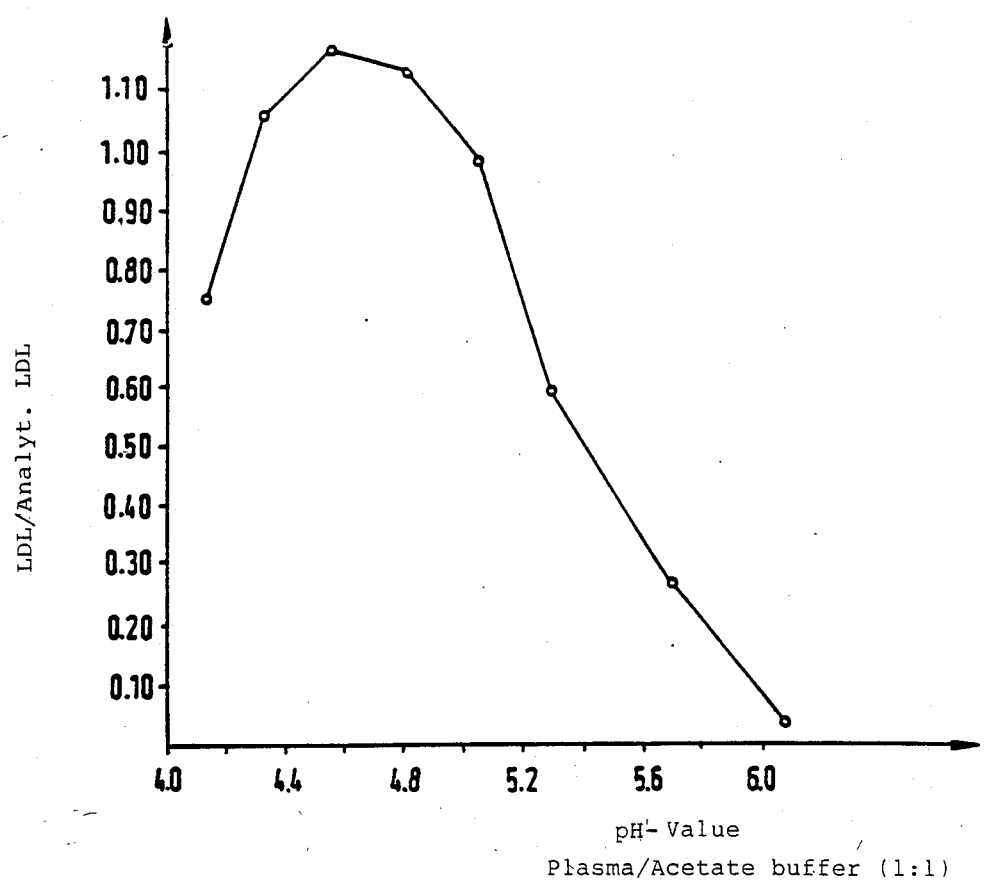
FIG. 12 shows the pH dependence of the LDL precipitation with the LDL-precipitating substance according to the invention.

The ability of the obtained product to precipitate LDL from human plasma was determined by the method described in Example 5C. The pH-dependence of the LDL-precipitation is shown in FIG. 12.

EXAMPLE 7

A heparin hydrolyzate prepared according to the directions given in Example 5A was reacted with succinic anhydride in a subsequent step. The objective of this step was the succinylation of the amine groups freed by the hydrolysis step by known methods. For this, 2 g of a heparin hydrolyzate (according to Example 5A) with a coagulation activity of 5.71 IU/ml (USP XX) was dissolved in 24 ml H$_2$O and reacted in portions with 600 mg succinic anhydride. The pH was maintained at 8.0 with 5 N NaOH. After the completion of the addition, the pH of the solution was adjusted to 7.5 and the solution dialyzed for two days against water. The product was precipitated with ethanol and the isolated precipitate was dried overnight at 60° in the vacuum drying cabinet.

The white product had a coagulation activity of 18.8 IU/mg (USP XX).

Figure 13:
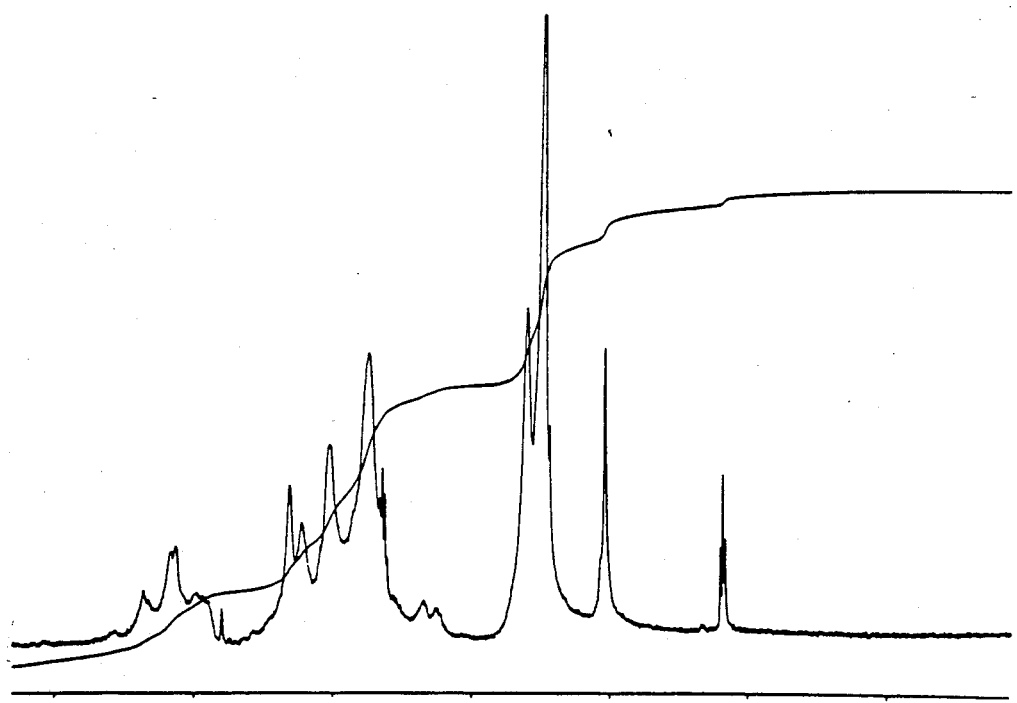
FIG. 13 demonstrates 400-MHz $^1$H-Spectrum of the LDL-precipitating substance.
Figure 14:
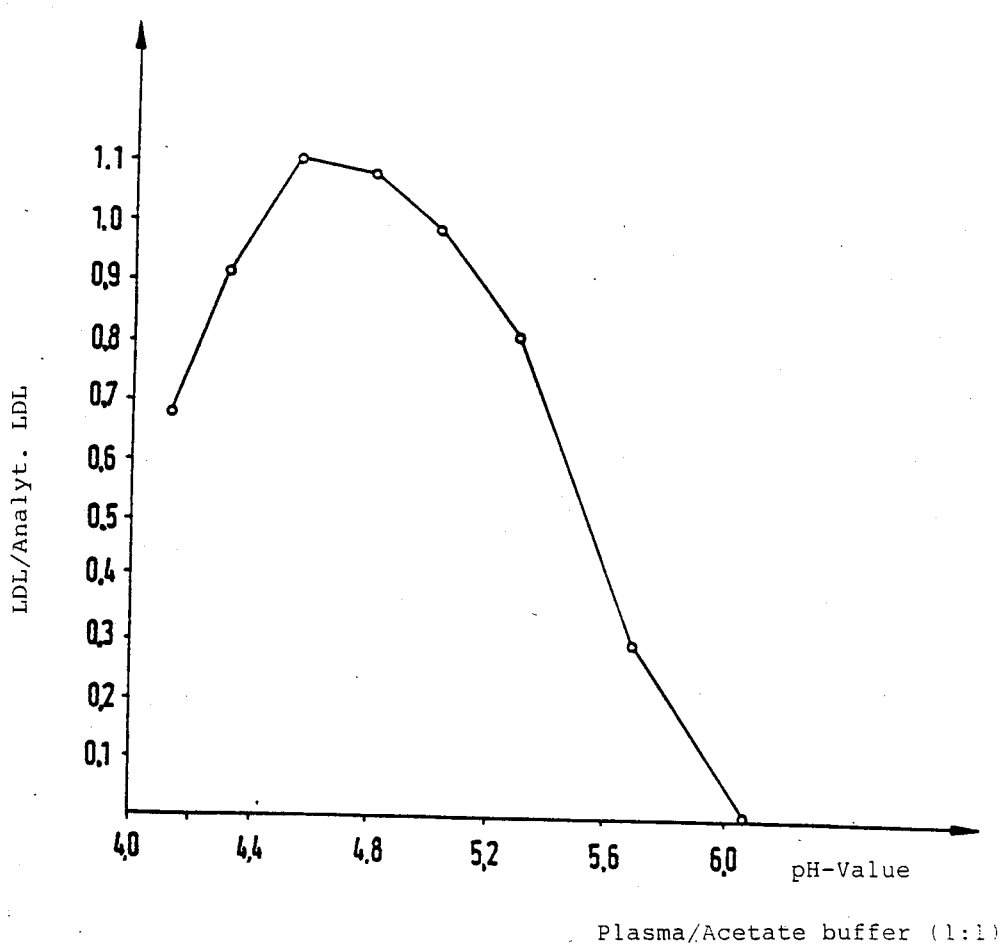
FIG. 14 shows the pH dependence of the LDL precipitation with the LDL-precipitating substance according to the invention.

FIG. 13 shows the 400-MHz $^1$H-spectrum of the product (50 mg/ml D$_2$O; internal standard: HDO;$\delta$=4.8 ppm rel. TMS). Several characteristics of the product relative to the starting material and heparin can be found in Table 3 below. The pH dependence of the LDL-precipitation furnished the curve shown in FIG. 14. The precipitation was performed under the conditions given in Example 5C.

TABLE 3

|  | Heparin | Heparin-hydrolyzate | Succinylated product |
| --- | --- | --- | --- |
| Free amine groups (umol/g) | 17.4 | 145 | 5.1 |
| Rate of cleavage of heparinase | 100% | 53% | 48% |
| Specific rotation $(\alpha)_D^{20}$ | +52.5° | +51° | +30.8° |
| Metachromatic effect (toluidine blue) | 1.00 | 0.85 | 0.73 |

While there have been described what are presently believed to be preferred embodiments of the invention, it will be apparent to a person skilled in the art that numerous changes can be made in the ingredients, conditions and proportions set forth in the foregoing embodiments without departing from the invention as described herein and as defined in the appended claims.

What is claimed is:

1. A method for the therapeutic treatment of a patient by the substantially selective precipitation of low density lipoproteins without the use of polyvalent cations which comprises administering to a volume of blood, plasma, or a solution of blood or plasma of the patient a low-density lipoprotein precipitating substance other than heparin having a coagulation activity greater than about 1 IU/mg at a pH between about 4 and 5.8 such that an anticoagulent effect associated with heparin is minimized or eliminated.

2. The method according to claim 1 wherein the low density lipoprotein precipitating substance is selected from the group consisting of hydrolyzed heparin, hydrolyzed heparin acylated at free amine groups, sulfated glycosamino glycan and sulfated polysaccharides.

3. The method according to claim 1 wherein the therapeutically effective amount is about 1 gram/liter.

4. A method for the therapeutic treatment of a patient by the substantially selective precipitation of low-density lipoproteins without the use of polyvalent cations which comprises administering to a volume of blood, plasma or a solution of blood or plasma of the patient a low density lipoprotein precipitating substance having a coagulation activity greater than about 1 IU/mg selected from the group consisting of hydrolyzed heparin, hydrolyzed heparin acylated at free amine groups, sulfated glycosamino glycan and sulfated polysaccharides at a pH in the range of about 4.0 to 5.8 such that an anticoagulent effect associated with heparin is minimized or eliminated.

5. The method according to claim 4 wherein the low density lipoprotein precipitating substance is administered in an amount of about 0.9 gram/liter.

6. The method according to claim 5 wherein said hydrolyzed heparin and said hydrolyzed heparin acylated at free amine groups are characterized by a coagulation activity of less than about 20 IU/mg and a low affinity to antithrombin III as compared to heparin.

7. The method according to claim 6 wherein the hydrolyzed heparin has a content of free amine groups of about 50 to 400 umol/g and the hydrolyzed heparin acylated at free amine groups has a content of free amine groups of about 2 to 10 $\mu$mol/g.

8. The method according to claim 4 wherein the low-density lipoprotein precipitating substance has an anticoagulent activity of less than about 35 IU/mg.

9. A method of selectively precipitating low-density lipoproteins without the use of polyvalent cations which comprises administering to a volume of blood, plasma or solutions containing blood or plasma a low density lipoprotein precipitating substance having a coagulation activity greater than about 1 IU/mg selected from the group consisting of the following:

(a) sodium salt of chondrolitin sulfate;
(b) sodium salt of heparin sulfate;
(c) sodium salt of dermatan sulfate;
(d) sodium pentosan polysulfate;
(e) mucopolysaccharide polysulfuric acid ester;
(f) heparinoid Bayer 5000 HDB-E;
(g) mucopolysaccharide polysulfuric acid ester;
(h) sodium salt of the polyanethol sulfonic acid;
(i) heparin derivatives prepared on a base of chitosan;
(j) heparinoids on a base of xylane;
(k) heparinoids derived from alginic acid;
(l) heparinoids on a base of cellulose sulfate;
(m) heparinoids on a base of sulfated N-carboxymethyl chitosan;
(n) synthetic heparinoids;

said method being performed at a pH between about 4 and 5.8 such that an anticoagulent effect associated with parin is minimized or eliminated.

10. The method according to claim 9 wherein the low-density lipoprotein precipitating substance has an anticoagulent activity of less than about 35 IU/mg.

11. The method according to claim 9 wherein the therapeutically effective amount is about 0.9 gram/liter.

12. The method according to claim 9 wherein the method is performed extracorporally.

13. The method according to claim 9 wherein the method is a diagnostic method.

14. A method for the therapeutic treatment of a patient by the substantially selective precipitation of low-density lipoproteins without the use of polyvalent cations which comprises administering to a volume of blood, plasma or solutions containing blood or plasma a low density lipoprotein precipitating substance having a coagulation activity greater than about 1 IU/mg selected from the group consisting of the following:

(a) sodium salt of chondroitin sulfate;
(b) sodium salt of heparin sulfate;

(c) sodium salt of dermatan sulfate;
(d) sodium pentosan polysulfate;
(e) mucopolysaccharide polysulfuric acid ester;
(f) heparinoid Bayer 5000 HDB-E;
(g) mucopolysaccharide polysulfuric acid ester;
(h) sodium salt of the polyanethol sulfonic acid;
(i) heparin derivatives prepared on a base of chitosan;
(j) heparinoids on a base of xylane;
(k) heparinoids derived from alginic acid;
(l) heparinoids on a base of cellulose sulfate;
(m) heparinoids on a base of sulfated N-carboxymethyl chitomsan;
(o) synthetic heparinoids;
(p) heparinoids on a base of dextran;
said method being performed at a pH between about 4 and 5.8 such than an anticoagulent effect associated with heparin is minimized or eliminated.

15. The method according to claim 14 wherein the method is performed extracorporally.

* * * * *